US010048270B2

(12) United States Patent
Berkelman

(10) Patent No.: US 10,048,270 B2
(45) Date of Patent: Aug. 14, 2018

(54) HCP ANTISERUM VALIDATION USING A NON-INTERFERING PROTEIN STAIN

(71) Applicant: Bio-Rad Laboratories, Inc., Hercules, CA (US)

(72) Inventor: Tom Berkelman, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 282 days.

(21) Appl. No.: 15/036,387

(22) PCT Filed: Nov. 12, 2014

(86) PCT No.: PCT/US2014/065297
§ 371 (c)(1),
(2) Date: May 12, 2016

(87) PCT Pub. No.: WO2015/073583
PCT Pub. Date: May 21, 2015

(65) Prior Publication Data
US 2016/0291033 A1    Oct. 6, 2016

Related U.S. Application Data

(60) Provisional application No. 61/903,234, filed on Nov. 12, 2013.

(51) Int. Cl.
| | |
|---|---|
| G01N 31/00 | (2006.01) |
| G01N 33/53 | (2006.01) |
| G01N 33/68 | (2006.01) |
| G01N 1/30 | (2006.01) |
| G01N 33/15 | (2006.01) |
| G06T 7/33 | (2017.01) |

(52) U.S. Cl.
CPC ........... *G01N 33/6842* (2013.01); *G01N 1/30* (2013.01); *G01N 33/15* (2013.01); *G01N 33/6803* (2013.01); *G06T 7/337* (2017.01); *G01N 2001/302* (2013.01)

(58) Field of Classification Search
None
See application file for complete search history.

(56) References Cited

U.S. PATENT DOCUMENTS

| | | | |
|---|---|---|---|
| 2003/0165989 A1* | 9/2003 | Au-Young | C07K 14/7158 435/7.1 |
| 2005/0214735 A1 | 9/2005 | Yonan et al. | |
| 2007/0281360 A1* | 12/2007 | Wolf | G01N 33/6839 436/86 |
| 2008/0108508 A1 | 5/2008 | Hermetter et al. | |
| 2008/0261249 A1* | 10/2008 | Wang | G01N 33/54306 435/7.92 |
| 2008/0261827 A1 | 10/2008 | Iwakura et al. | |
| 2012/0009603 A1 | 1/2012 | Della et al. | |
| 2013/0029377 A1 | 1/2013 | Caparon et al. | |
| 2013/0287772 A1 | 10/2013 | Halbert et al. | |

FOREIGN PATENT DOCUMENTS

| | | |
|---|---|---|
| CN | 102707058 A | 10/2012 |
| WO | 2007/141510 A1 | 12/2007 |

OTHER PUBLICATIONS

International Search Report and Written Opinion dated Feb. 6, 2015 in PCT/US14/65297, 16 pages.
Rellahan, Barbara, "Process Related Impurities and their Impact on Product Quality—An FDA Perspective and Recommendations (With Emphasis on Host Cell Protein (HCP) Impurities)," 2013, [online], [retrieved on Dec. 27, 2016]. Retrieved from the internet <    URL:https://c.ymcdn.com/sites/casss.site-ym.com/resource/resmgr/WCBP_Speaker_Slides/2013_WCBP_Rellahan_Barbara.pdf> 35 pages.
Savino, Edward, et al., "Development of an In-House, Process-Specific ELISA for Detecting HCP in a Therapeutic Antibody, Part 1," Mar. 2011, BioProcess International, 9 pages.
Wang, Xing, et al., "Host Cell Proteins in Biologics Development Identification Quantitation and Risk Assessment," Biotechnology and Bioengineering, Jun. 15, 2009, vol. 103, No. 3, pp. 446-458.
Extended European Search Report dated May 12, 2017 in EP Appln. 14862641.9, 8 pages.
Berkelman, T. et al.; "Reliable, streamlined 2D western blot workflow for evaluation of antibodies developed for detection of host cell proteins"; *Bioradiations*; May 17, 2013; pp. 1-11.
Berkelman, T. et al.; "Enhanced 2-D electrophoresis and western blotting workflow for reliable evaluations of anti-HCP antibodies"; *Bioprocess International 2013*; vol. 11, No. 8; Sep. 2013; pp. 50-61.
Wolter, T. et al.; "Assays for controlling host-cell impurities in biopharmaceuticals"; *BioProcess International*; Feb. 2005; pp. 40-46.
Berkelman, T. et al.; "2-D western blotting for evaluation of antibodies developed of host cell protein"; *Methods Mol. Biol.*; vol. 1295; 2015; pp. 393-414.
First Chinese Office Action dated May 12, 2017 in CN Appln. 201480036585.0, 19 pages.
Hunter, A. et al.; "Separation of Product Associating *E. coli* Host Cell Proteins OppA and DppA from Recombinant Apolipoprotein A-I$_{milano}$ in an Industrial HIC Unit Operation"; *Biotechnol. Prog.*; vol. 25, No. 2; Mar. 16, 2009; pp. 446-453.
Unknown; "Experimental steps and key analysis of western blot"; *Baidu Wenku*; Mar. 28, 2013; pp. 1-15.
Basu S. et al.; "AKT Phosphorylates the Yes-Associated protein, YAP, to Induce Interaction with 14-3-3 and Attenuation of p73-Mediated Apoptosis"; *Molecular Cell*; vol. 11; Jan. 31, 2003; pp. 11-23.

* cited by examiner

*Primary Examiner* — Lisa V Cook
(74) *Attorney, Agent, or Firm* — Kilpatrick Townsend and Stockton LLP

(57) ABSTRACT

Methods and compositions are provided for validating immunological detection reagents for use in detecting contaminating host cell components in a biological preparation.

20 Claims, 5 Drawing Sheets

HCP ANTISERUM VALIDATION USING A NON-INTERFERING PROTEIN STAIN

CROSS-REFERENCE TO RELATED APPLICATION

This application is a U.S. National Phase Application of PCT/US2014/065297, filed Nov. 12, 2014, which application claims priority to U.S. Provisional Application No. 61/903,234, filed Nov. 12, 2013, the contents of each of which are hereby incorporated by reference in the entirety for all purposes.

BACKGROUND OF THE INVENTION

Biologic drugs, or biologics, such as therapeutic proteins are generally derived from a host cell. For example, a host cell can be genetically engineered to produce a therapeutic recombinant protein. As another example, the biologic can be an endogenous non-recombinant protein. The host cell can be harvested and lysed, and the biologic can be purified from contaminating host cell constituents through a variety of processes. Alternately, the biologic can be secreted by the host cell into conditioned media, the media harvested, and the biologic purified from contaminants in the conditioned media. Host cell contaminants include host cell proteins (HCP).

HCP contaminants can have an undesirable effect even at very low concentration. For example, they can interfere with the function of the biologic. As another example, HCP contaminants can induce an allergic response or rejection of the biologic by the immune system. It is therefore believed that removal of all, substantially all, or most HCP contamination can reduce undesirable effects.

Accordingly, quality control testing of biologics often includes a test to show that HCP contaminants have been sufficiently removed such that HCP contamination is at a low, permissible level. Detection of low level contaminants can be performed using immunochemical assays, which generally have low detection limits. For example, ELISA can be used with a polyclonal antibody mixture that has been developed to have reactivity against a wide range of potential HCPs. Development of the polyclonal antibody mixture requires optimization of the number of potential targets recognized and the sensitivity and specificity of the assay. Polyclonal antibody mixtures thus need to be validated by demonstrating they detect sufficient numbers of HCPs with acceptable sensitivity and specificity prior to their adoption.

HCP assay validation can be performed by two dimensional (2-D) electrophoresis and western blotting. For example, two aliquots of a sample can each be separated by size and isoelectric point on two different 2-D electrophoresis gels. One gel can be stained with a highly sensitive total protein stain such as a silver, zinc, copper, or Coomassie G-250 stain, and the number of stained spots observed to determine an approximate number of total proteins in the sample. The second gel can be transferred to a western blot membrane and probed with a candidate polyclonal antibody mixture. A comparison between the detected proteins via total protein stain and western blot allows the specificity and sensitivity of the antibody mixture to be determined.

Therefore, the technique requires the ability to determine with reasonable confidence whether or not an identified feature/spot between the gel image and the blot image correspond to the same protein. In particular, a match is assumed when a feature is in the same relative position in both the gel and blot images. However, the assignment of a match can be complicated when the images, or individual features within the images, are not in registry with each other. Lack of registry between the gel image and the blot image, or features therein, can occur because of inconsistencies in electrophoresis, transfer, and staining, and the images can be of different size due to shrinkage or swelling of the gel. These sources of inconsistency, and others, can cause incorrect or ambiguous matching.

BRIEF SUMMARY OF THE INVENTION

This invention provides an improved method for validation of polyclonal antibody mixtures for detection of contaminating host cell proteins (HCPs) in a biological sample. In some embodiments, the method dispenses with the need for separate 2-D gels for total protein staining and western blot detection.

In some embodiments, the invention provides a method for validating an immunological detection reagent comprising a polyclonal antibody mixture for use in detection of contaminating host cell proteins (HCPs) in a biological sample, the method comprising: providing a biological sample containing HCPs; separating the HCPs by apparent molecular weight and isoelectric point; transferring the separated HCPs to a membrane, thereby producing membrane-bound HCPs; staining membrane-bound HCPs using a non-interfering total protein stain, thereby detecting host cell protein (HCP) positions on the membrane with the non-interfering total protein stain; observing and recording the HCP positions on the membrane detected by the non-interfering total protein stain; contacting the membrane with the polyclonal antibody mixture, thereby binding antibodies from the polyclonal antibody mixture to the membrane-bound HCPs; detecting antibodies from the polyclonal antibody mixture bound to the membrane, thereby detecting HCP positions on the membrane with the polyclonal antibody mixture; observing and recording the HCP positions on the membrane detected by the polyclonal antibody mixture; and comparing the HCP positions detected by the non-interfering total protein stain to the positions detected by the polyclonal antibody mixture, thereby validating the polyclonal antibody mixture for use in detection of contaminating host cell proteins HCPs in a biological sample.

In some aspects, the non-interfering total protein stain is substantially removed from the membrane prior to contacting the membrane with a polyclonal antibody mixture. For example, the non-interfering total protein stain can be substantially removed from the membrane by contacting the membrane with a blocking solution. In some cases, the blocking solution comprises a buffered solution of serum albumin, gelatin, or casein; serum or non-fat milk; or a protein free blocking solution containing hydrophilic or amphiphilic synthetic polymers.

In some aspects, the non-interfering total protein stain detects HCP positions that contain at least about 0.25 ng to at least about 1, 2, 5, or 10 ng of protein on a western blot membrane. In some cases, the non-interfering total protein stain comprises an metalorganic chelate. For example, the metalorganic chelate can comprise ruthenium. In some cases, the metalorganic chelate comprising ruthenium is SYPRO Ruby protein stain. In some cases, the metalorganic chelate comprising ruthenium is a sulfonated derivative of ruthenium II tris (bathophenanthroline). For example, the sulfonated derivative of ruthenium II tris (bathophenanthroline) can be ruthenium II tris (bathophenanthroline disulfonate).

In some aspects, the non-interfering total protein stain comprises an azaphilone that reacts with primary amines to produce fluorescent compounds. For example, the azaphilone can be epicocconone.

In some aspects, the observing the HCP positions on the membrane detected by the non-interfering total protein stain is performed by illuminating the membrane with electromagnetic radiation (e.g., ultraviolet, visible, or infrared light) and detecting fluorescence.

In some aspects, the detecting antibodies from the polyclonal antibody mixture bound to the membrane comprises contacting the membrane with a secondary detection reagent to detect bound antibodies. In some cases, the secondary detection reagent is a secondary antibody. In some cases, the secondary antibody is labeled, for example, the secondary antibody can be labeled with an enzyme, a fluorophore, a radioactive isotope, biotin, avidin, or streptavidin. The enzyme can be, for example, horseradish peroxidase or alkaline phosphatase. The fluorophore can be, for example, a cyanine dye, a DyLight dye, an Alexa Fluor dye, a fluorescent nanoparticle, or a fluorescent protein.

In some aspects, the observing the HCP positions on the membrane detected by the polyclonal antibody mixture is performed by contacting the membrane with a chemiluminescent substrate and recording chemiluminescence. In some cases, the membrane is further contacted with a chemiluminescence enhancer, for example, the enhancer can be 3-(phenothiazin-10-yl)propane-1-sulfonate).

In some aspects, the HCP positions detected by the non-interfering total protein stain or the polyclonal antibody mixture are observed with a charge-coupled device (CCD)- or complementary metal-oxide-semiconductor (CMOS)-based camera.

In some aspects, the HCP positions detected by the non-interfering total protein stain and the polyclonal antibody mixture are observed and recorded using an imaging system. For example, the imaging system can comprise a computer, a CCD or CMOS camera, and software for observing and recording HCP positions detected by the non-interfering total protein stain and the polyclonal antibody mixture.

In any of the foregoing embodiments, aspects, cases or examples, the comparing can comprise; matching the HCP positions detected by the non-interfering total protein stain to the HCP positions detected by the polyclonal antibody mixture, wherein an HCP position is matched when they are in the same or an equivalent position on the western blot membrane; and determining a match rate. In some cases, the match rate is the number of HCP positions detected by the polyclonal antibody mixture divided by the total number of HCP positions detectable by either the polyclonal antibody mixture or the non-interfering total protein stain. In some cases, the polyclonal antibody mixture is validated if the match rate is at least about 0.2, 0.47, 0.5, or 0.75, or is about 1.

In some cases, the imaging system comprises means for comparing the HCP positions detected by the non-interfering total protein stain to the HCP positions detected by the polyclonal antibody mixture.

In some cases, the imaging system comprises means for matching HCP positions detected by the non-interfering total protein stain with HCP positions detected by the polyclonal antibody mixture, thereby determining a number of matched HCP positions. In some cases, the imaging system can further comprise means for comparing the number of matched HCP positions to the HCP positions detected by the non-interfering total protein stain.

In any of the foregoing embodiments, aspects, cases or examples, the polyclonal antibody mixture can be validated if the ratio of HCP positions detected by the polyclonal antibody mixture to total HCP positions detected by either the non-interfering total protein stain or the polyclonal antibody mixture is at least about 0.2, 0.47, 0.5, or 0.75, or is about 1.

DETAILED DESCRIPTION OF THE INVENTION

I. Definitions

Figure 1:
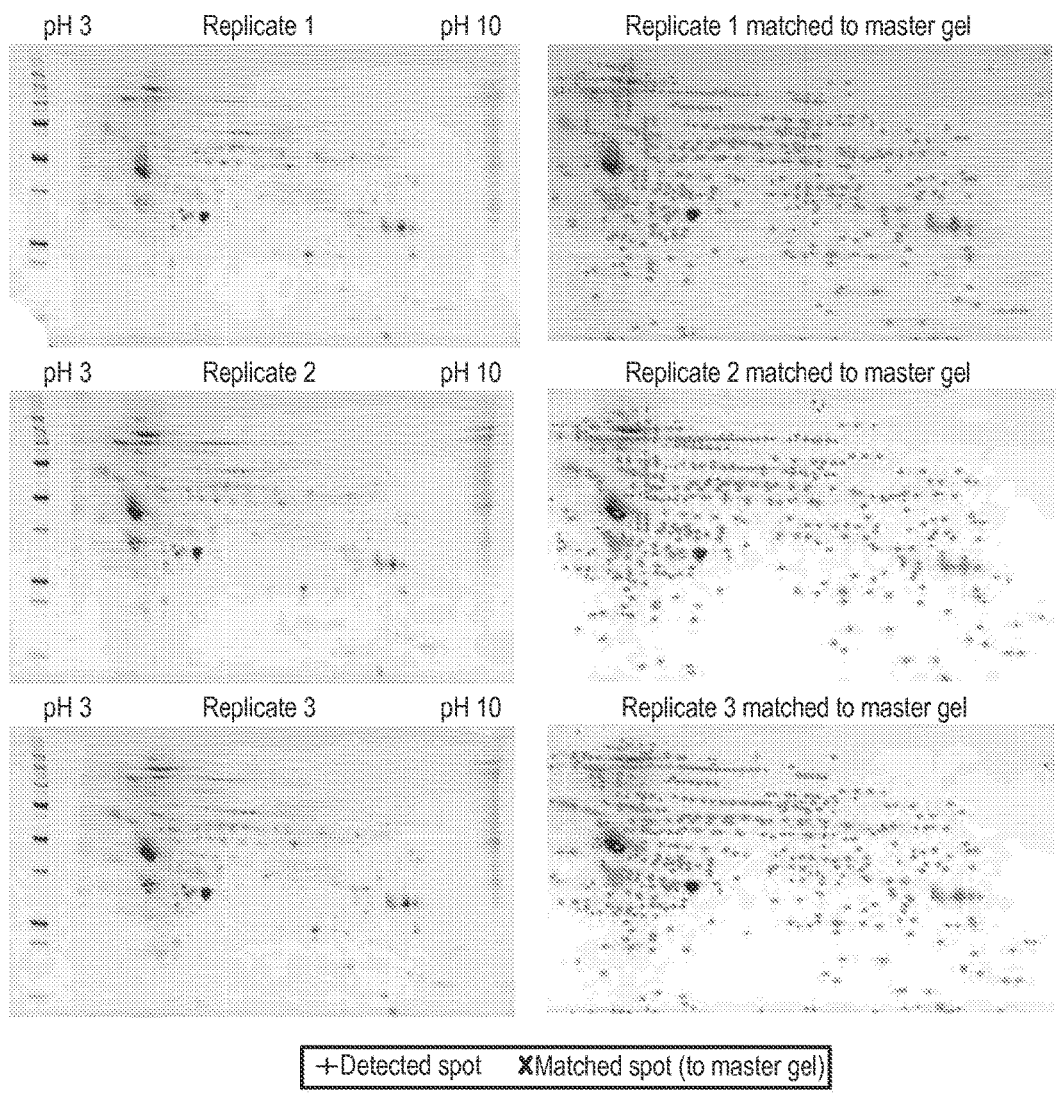
FIG. 1 depicts potential variability between replicate 2DE gels. Identical conditions were used to resolve CHO secreted protein sample by 2DE in parallel followed by total protein staining with Oriole™ fluorescent gel stain (left panels). PDQuest™ 2-D analysis software was used for spot counting as well as matching the 2DE replicates against a reference 'master gel' and to each other (right panels and bottom table).

As used in this specification and the appended claims, the singular forms "a," "an," and "the" include plural reference unless the context clearly dictates otherwise.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY Mannual, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

As used herein, the phrases "host cell protein" (HCP), "host cell proteins" (HCPs) and the like, refer to contaminating host cell components (e.g., proteins) that are present in a biologic preparation. HCPs can be detected by a variety of methods including, but not limited to, immunological detection, or the use of a total protein stain.

As used herein "host cell protein positions," or "HCP positions" refers to the physical positions of a detected host cell protein in a gel, or on a membrane, in which proteins are physically separated according to one or more physiochemical properties, such as apparent molecular weight (e.g., size) and/or isoelectric point.

HCP positions are "matched" between two different analyses when an HCP is detected at the same position in two different separations (e.g., two different polyacrylamide gels, two different membranes, or a gel and a membrane) or according to two or different detection regimes (e.g., a protein detected at the same position by total protein stain and immunological detection).

The term "match rate," as used herein, refers to the ratio of HCP positions on a membrane that are detected by immunological detection over HCP positions detected by either total protein stain or immunological detection. Typically, matched HCP positions detected by both total protein stain and immunological detection are counted once in the denominator. An HCP position is matched when it occupies the same position on a membrane. In an exemplary embodiment, the match rate is calculated as immunologically detected positions divided by positions detected by total protein stain and positions detected immunologically (i.e., number of immunodetected features divided by the number of all detected features). In some cases, the number of all detected features is such that matched features detected by both immunodetection and total protein stain are only counted once in the denominator. Alternatively, the match rate can be calculated by dividing the total number of HCP positions detected immunologically by the total number of HCP positions detected by total protein stain. As yet another alternative, the match rate can be calculated by dividing the total number of HCP positions detected by total protein stain by the total number of HCP positions detected immunologically.

As used herein, the phrase "immunological detection" refers to detection of a target antigen with an antibody, or detection of a plurality of target antigens with a plurality of antibodies or antibody fragments. Immunological detection can include, but is not limited to, ELISA or western blot detection methods.

As used herein, the phrase "non-interfering total protein stain" refers to a non-antibody detection reagent that binds to proteins to enable their detection and does not interfere, or does not substantially interfere, with subsequent immunological detection reagents. In some cases, the non-interfering total protein stain can be removed, or substantially removed, after detecting proteins with the stain and before immunological detection. For example, in some cases, at least about 50%, 60%, 65%, 70%, 75%, 80%, 85%, 90%, 95%, 99%, or more of the non-interfering total protein stain can be removed after detecting proteins with the stain and before immunological detection. In other cases, the non-interfering total protein stain can be inactivated, or substantially inactivated, after detecting proteins with the stain and before immunological detection. In yet other cases, the non-interfering total protein stain can remain bound to the detected proteins and yet still not interfere with subsequent immunological detection. As an example, in some cases, the non-interfering total protein stain can exhibit little or no effect on binding of antibodies to the detected proteins, exhibit little or no detectable effect on detection of bound antibodies, or exhibit little or no detectable effect on fluorescence, chemiluminescence, chromogenic, or radiographic imaging of immunologically detected proteins on a gel or membrane after contact with the total protein stain. An exemplary non-interfering protein stain is SYPRO Ruby. In contrast, an example of a total protein stain that is interfering is Coomassie Brilliant Blue (e.g., Coomassie Brilliant Blue R-250 or Coomassie Brilliant Blue G-250).

Non-interfering total protein stains can be identified by methods known in the art. For example, host cell proteins, or a suitable alternate such as a complex protein mixture, e.g., rat liver lysate, can be separated on a gel, e.g., by two-dimensional gel electrophoresis, and blotted onto a membrane. The membrane-bound host cell proteins, or alternate, can then be detected by contacting the membrane with a candidate total protein stain. After contacting the membrane with total protein stain and detecting membrane bound proteins, the membrane-bound proteins can be immunologically detected with a polyclonal antibody mixture. In some cases, the membrane-bound proteins can be immunologically detected with a polyclonal antibody mixture known to detect essentially all, or substantially all, proteins bound to the membrane. Non-interfering total protein stains can then be identified as those stains in which at least about 20%, 30%, 40%, 50%, 60%, 70%, 80%, 90%, 95%, 99%, substantially all, or all of the membrane bound proteins detected by the total protein stain are also detected by the subsequent immunological detection.

Alternatively, non-interfering total protein stains can be identified by comparing (1) immunological detection of a blot that has been not been previously stained by a candidate total protein stain to (2) immunological detection of a blot that has been previously stained by the total protein stain. For example, two aliquots of a complex protein mixture can be separated on two different gels in parallel (e.g., by 2D-electrophoresis) and the proteins blotted onto two different membranes. Membrane-bound proteins can be detected on one membrane by staining the membrane with a candidate total protein stain, followed by immunological detection. Membrane-bound proteins can be detected on the other membrane by immunological detection. Non-interfering total protein stains can then be identified as those stains in which at least about 20%, 30%, 40%, 50%, 60%, 70%, 80%, 90%, 95%, 99%, substantially all, or all of the membrane bound proteins detected by (1) are also detected by (2). In some cases, the comparison is between (2) and an expected number of detected proteins, and the non-interfering total protein stain is identified as a stain in which at least about 20%, 30%, 40%, 50%, 60%, 70%, 80%, 90%, 95%, 99%, substantially all, or all of the expected membrane bound proteins are detected immunologically on a blot that has been previously stained by the candidate total protein stain.

As used herein, the phrase "antibody" refers to one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An "antibody" functions as a binding protein and is structurally defined as comprising an amino acid sequence from or derived from the framework region of an immunoglobulin encoding gene of an animal producing antibodies.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The term "antibody" as used herein includes antibody fragments that retain binding specificity. For example, there are a number of well characterized antibody fragments. Thus, for example, pepsin digests an antibody C-terminal to the disulfide linkages in the hinge region to produce F(ab)'$_2$, a dimer of Fab which itself is a light chain joined to VH-CH1 by a disulfide bond. The F(ab)'$_2$ may be reduced under mild conditions to break the disulfide linkage in the hinge region thereby converting the F(ab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification of whole antibodies or synthesized using recombinant DNA methodologies.

An "isotype" is a class of antibodies defined by the heavy chain constant region. Immunoglobulin genes include the kappa, lambda, alpha, gamma, delta, epsilon, and mu constant region genes. Light chains are classified as either kappa or lambda. Heavy chains are classified as gamma, mu, alpha, delta, or epsilon, which in turn define the isotype classes, IgG, IgM, IgA, IgD and IgE, respectively.

Antibodies include $V_H$-$V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ which may be expressed from a nucleic acid including $V_H$- and $V_L$- encoding sequences either joined directly or joined by a peptide-encoding linker (e.g., Huston, et al. *Proc. Nat. Acad. Sci. USA*, 85:5879-5883, 1988). While the $V_H$ and $V_L$ are connected to each as a single polypeptide chain, the $V_H$ and $V_L$ domains associate non-covalently. Alternatively, the antibody can be another fragment. Other fragments can also be generated, e.g., using recombinant techniques, as soluble proteins or as fragments obtained from display methods. Antibodies can also include diantibodies and miniantibodies. Antibodies of the invention also include heavy chain dimers, such as antibodies from camelids.

A "polyclonal antibody" refers to refers to a preparation of antibodies, raised against a single antigen, with different binding specificities and affinities. A "polyclonal antibody mixture" refers to a mixture of polyclonal antibodies, each raised against a single antigen. Alternatively, a "polyclonal antibody mixture" can refer to a mixture of polyclonal antibodies derived from the serum of an animal that has been inoculated with a mixture of antigens. For example, the "polyclonal antibody mixture" can refer to a mixture of polyclonal antibodies obtained from the serum of an animal that has been inoculated with a preparation containing host cell proteins.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, *Bioconjugate Techniques* 1996, Academic Press, Inc., San Diego.

A "labeled" molecule (e.g., nucleic acid, protein, or antibody) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

II. Methods

Described herein are methods for validating an immunological detection reagent containing a polyclonal antibody mixture for detecting contaminating HCPs. The methods employ separating HCPs in a sample (e.g., separating by gel electrophoresis, or gel electrophoresis and membrane blotting), detecting the HCPs with a total protein stain that does not interfere with subsequent immunological detection, and immunological detection of the HCPs with the polyclonal antibody mixture.

The methods can further employ comparison of the HCPs detected by the total protein stain to those detected by the polyclonal antibody mixture. The comparison can be performed by determining a match rate. In some cases, the comparison can be performed by observing HCP positions obtained via the total protein stain and comparing these positions to immunologically detected HCP positions. In some cases, the immunological detection reagent containing a polyclonal antibody mixture is validated when the match rate is high (e.g., at least about 0.2, 0.3, 0.4, 0.47, 0.5, 0.6, 0.7, 0.8, 0.9, or higher). In some cases, the immunological detection reagent is validated when the number of immunologically detected HCP positions is a substantial proportion (e.g., at least about 0.2, 0.3, 0.4, 0.47, 0.5, 0.6, 0.7, 0.8, 0.9, or higher) of total HCP positions (e.g., where total HCP positions are those detected by total protein stain or immunological methods, wherein matched positions are counted once). In some cases, the immunological detection reagent is validated when the number of immunologically detected HCP positions is a substantial proportion (e.g., at least about 0.2, 0.3, 0.4, 0.47, 0.5, 0.6, 0.7, 0.8, 0.9, or higher) of HCP positions detected by total protein stain.

In some embodiments, the methods include: providing a biological sample containing HCPs; separating the HCPs by apparent molecular weight and isoelectric point; transferring the separated HCPs to a membrane, thereby producing membrane-bound HCPs; staining the membrane-bound HCPs using a non-interfering total protein stain, thereby detecting HCP positions; observing and recording the HCP positions on the membrane detected by the non-interfering total protein stain; contacting the membrane with a polyclonal antibody mixture, thereby binding antibodies from the polyclonal antibody mixture to the membrane-bound HCPs; detecting the antibodies from the polyclonal antibody mixture bound to the membrane, thereby detecting HCP positions on the membrane with the polyclonal antibody mixture; observing and recording the HCP positions on the membrane detected by the polyclonal antibody mixture; and, comparing the HCP positions detected by the non-interfering total protein stain to the positions detected by the polyclonal antibody mixture, thereby validating the polyclonal antibody mixture for use in detection of contaminating host cell proteins in a biological sample. In some cases, the polyclonal antibody mixture is validated when it detects at least about 20%, 25%, 30%, 40%, 45%, 50%, 55%, 60%, 65%, 70%, 75%, 80%, 85%, 90%, 95%, 97.5%, or 99%, or more of the total proteins detected by the non-interfering total protein stain.

Alternatively, the comparison can be made by determining a ratio of HCP positions detected by the polyclonal antibody mixture to total HCP positions detected (e.g., HCP positions detected by either the polyclonal antibody mixture or the total protein stain, wherein positions detected by both methods are counted once). As another alternative, the ratio of the number of positions detected by the polyclonal antibody mixture can to the number of positions detected by the total protein can be determined. For example, the number of positions can be observed and recorded and compared without regard to determining which positions are matched between the different detection methods. As yet another alternative, the ratio of the number of positions detected by the polyclonal antibody mixture to the number of positions detected by detected by either method (e.g., to the number of positions detected by total protein stain or immunological detection) can be determined. For example, the number of positions can be observed and recorded and compared without regard to determining which positions are matched between the different detection methods. In some cases, the polyclonal antibody mixture is validated when the determined ration is at least about 0.2, 0.3, 0.4, 0.47, 0.5, 0.6, 0.7, 0.8, 0.9, 0.95, or higher.

The provided biological sample containing HCPs can be obtained via any method known in the art. In some cases, the biological sample is blood, tissue, or serum from the organism from which a host cell is derived. For example, the biological sample can be human, cow, rat, mouse, rabbit, hamster, or chicken blood, tissue, or serum. In other cases, the biological sample is a host cell. In some cases, the biological sample is extracted, concentrated, or purified to obtain a purified or enriched sample of HCPs.

In some cases, the biological sample containing HCPs can be obtained as conditioned culture media. For example, the biological sample can be cell-free, or substantially cell-free, culture supernatant or filtrate. In some cases, a biologic can be secreted into the culture supernatant of a cell transformed with a recombinant expression cassette. A polyclonal antibody mixture for detection of contaminating HCPs can, for example, then be validated using a biological sample that is, contains, or is derived from, culture supernatant of a cell that is not transformed with the recombinant expression cassette. In some cases, the culture supernatant can be further extracted, concentrated, or purified to obtain a purified or enriched sample of HCPs.

Methods for purifying host cell proteins from a biological sample, or enriching a biological sample in host cell proteins, are well known in the art. For example, the biological sample can be treated to separate, degrade, or remove nucleic acids. Exemplary methods can additionally, or alternatively, include, but are not limited to, contacting the biological sample with an endonuclease or an exonuclease, centrifuging the sample, filtering the sample, dialyzing the sample, concentrating the sample, precipitating HCPs in the sample, such as by trichloroacetic acid and/or acetone precipitation, or a combination thereof. In some cases, the biological sample is treated according to purification or enrichment steps the correspond to the process for purification of the biologic in order to generate a protein population that is representative of the HCPs present during particular process steps.

In some cases, a fresh biological sample is obtained prior to separation of HCPs and provided. For example, the biological sample can be obtained seconds, minutes, hours, or 1 or 2 days before separation of HCPs and provided. In other cases, the biological sample is obtained and stored for a period of time (e.g., a few days, a week, a few weeks, a month, or longer). In some cases, the biological sample is stabilized prior to or during the storage to prevent degradation or loss of HCPs. Stabilization methods are well known in the art. Exemplary stabilization methods include, but are not limited to storing the sample at less than room temperature (e.g., about 4° C.), freezing the sample, extracting, inhibiting, or inactivating proteases in the sample, purifying HCPs in the sample away from components that increase degradation or loss of HCPs, or a combination thereof.

HCPs can be separated according to a variety of methods well-known in the art. For example, HCPs can be separated by 2-D gel electrophoresis. 2-D gel electrophoresis can include separation of proteins by isoelectric point and apparent molecular weight (i.e., size) in a gel, such as a polyacrylamide gel. In some cases, the proteins are first separated by isoelectric point and then size. In other cases, the proteins are separated by size and then isoelectric point.

Separated HCPs can be transferred to a membrane using any method known in the art. For example, HCPs can be blotted onto the membrane. Blotting can be performed by contacting the separated proteins to the membrane. For example, the HCPs can be separated in a gel (e.g., a polyacrylamide gel such as an SDS or LDS polyacrylamide gel), and the gel contacted with the membrane. In some cases, the blotting further includes using capillary action, vacuum, pressure, or electromagnetic force to move HCPs from the gel to the membrane. For example, the gel can be contacted with the membrane and an electric field applied to move the HCPs from the gel to the membrane. In some cases, where an electromagnetic force is utilized to move HCPs from the gel to the membrane, a buffer is utilized to ensure that the protein has an appropriate charge such that it moves toward the membrane in the presence of the applied electric field. For example, the gel can contain a buffer at a pH such that the majority of proteins are either positively or negatively charged.

Transferred proteins can be detected on the membrane by use of a total protein stain. In some embodiments, e.g., when the membrane will be used for subsequent immunological detection of transferred proteins, the use of a non-interfering total protein stain is preferred. Total protein stains are known in the art and include, those described herein. In some cases, the total protein stain provides a fluorescent signal, and HCP positions are detected using the total protein stain by illuminating the membrane with light at a specified wavelength and detecting an emitted fluorescent signal at a longer wavelength. In some cases, the fluorescent signal is detected using an imaging device or a scanner. The imaging device or scanner can be equipped with one or more light sources such as a xenon lamp, LED (e.g., multicolor LED), or one or more lasers. The imaging device or scanner can include one or more excitation and/or emission filters, diffraction gratings, and the like for providing a suitable excitation source and emission detector. The imaging device can be equipped with one or more light sensitive detectors, including but not limited to: a CCD detector, a CMOS detector, a photomultiplier tube, a photodiode, an avalanche photodiode, film, or the like. The imaging device can contain a computer system, such as, for example, a computer system as described herein.

In some embodiments, the membrane can be blocked by contacting the membrane with a suitable blocking agent for a suitable period of time. Suitable periods of time for contacting the membrane with the blocking agent include any time that is at least about 1 minute, preferably at least 10 minutes, 15 minutes, or 30 minutes, more preferably at least about 1 or 2 hours, or more. Generally blocking is performed after total protein stain detection. In some embodiments, the blocking step is useful for both blocking and removal of all, substantially all, or a sufficient amount of total protein stain such that interference with subsequent immunological detection is reduced, substantially reduced, or eliminated. In some cases, the blocking is performed in multiple steps, for example, a membrane can be contacted with blocking agent for a period of time, optionally washed or rinsed, and then contacted with additional blocking agent.

In some embodiments, the blocked membrane can then be incubated with an immunological detection reagent (e.g. a polyclonal antibody mixture) and HCP positions thereby detected. Generally, the incubation is performed for a suitable period of time to enable binding of members of the polyclonal antibody mixture to target proteins. Suitable periods of time for incubating the membrane with the immunological detection reagent include any time that is at least about 1 minute, preferably at least 10 minutes, 15 minutes, or 30 minutes, more preferably at least about 1 or 2 hours, or more. In some cases, the incubating is performed overnight. In other cases, overnight incubation can result in a higher background level and is preferably avoided. Methods for use of immunological detection reagents to detect proteins immobilized on a blocked membrane are well-known in the art, and further variations can be readily determined by those of skill in the art.

Also provided herein are methods for washing unbound immunological detection reagents away. In some embodiments, after incubating the immunological detection reagent with the blocked membrane, unbound detection reagent is removed by washing. Washing can be performed by a variety of methods known in the art. For example, the membrane can be incubated in phosphate buffered saline, optionally in the presence of a non-denaturing detergent for approximately 15 minutes. In some cases, the washing can be performed 1, 2, 3, 4, or more times.

In some cases, the bound immunological detection reagent can then be detected. For example, if the immunological detection reagent has been labeled with a detectable enzyme or fluorophore, the presence of the enzyme or fluorophore can be detected, and thereby the HCP positions observed. Alternatively, a secondary immunological detection reagent (e.g., a secondary antibody) can be used to detect the presence of the first immunological detection reagent. For example, if the first immunological detection reagent is a mouse polyclonal antibody mixture, the secondary antibody can be an anti-mouse antibody or anti-mouse antibody mixture. Generally, the secondary antibody is labeled with a detectable label such as a fluorophore, a ligand, or an enzyme. Exemplary labels for secondary antibodies include biotin, avidin, streptavidin, fluorescein, or horseradish peroxidase.

In some embodiments, the secondary antibody is labeled with horseradish peroxidase and detected using a chemiluminescent substrate. Chemiluminescent substrates are well known in the art and include, without limitation, luminol. In some cases, the chemiluminescent signal is enhanced by the addition of an enhancer. An exemplary chemiluminescent enhancer is p-iodophenol. As another example, the chemiluminescent enhancer 3-(phenothiazin-10-yl)propane-l-sulfonate) can be utilized. Further chemiluminescent enhancers are known in the art such as those described in U.S. Pat. Nos.: 7,855,287; 5,171,668; 4,729,950; 6,432,662; and 8,123,136.

Suitable fluorophores for detection of the bound immunological detection reagent include any fluorophore known in the art for detection of immunological detection reagents such as antibodies. For example, the fluorophore can be a cyanine dye (e.g., Cy2, Cy3, Cy3B, Cy3.5, Cy5, Cy5.5, or Cy7), a DyLight dye (e.g., DyLight 350, DyLight 405, DyLight 488, DyLight 550, DyLight 594, DyLight 633, DyLight 650, DyLight 680, DyLight 755, DyLight 880), an Alexa Fluor Dye (e.g., Alexa Fluor 350, Alexa Fluor 405, Alexa Fluor 430, Alexa Fluor 488, Alexa Fluor 514, Alexa Fluor 532, Alexa Fluor 546, Alexa Fluor 555, Alexa Fluor 568, Alexa Fluor 594, Alexa Fluor 610, Alexa Fluor 647, Alexa Fluor 660, Alexa Fluor 680, Alexa Fluor 700, Alexa Fluor 750, or Alexa Fluor 790), a xanthene dye (e.g., fluorescein, TAMRA, or Texas Red), a fluorescent nanoparticle, or a fluorescent protein (e.g., green, yellow, blue, or red fluorescent protein, mCherry, or phycoerythrin).

The secondary antibody, can be incubated with the membrane, washed to remove unbound secondary antibody, and visualized to thereby detect the HCP positions. As described above, the positions can be observed using an scanning or imaging device. In some cases the scanning or imaging device is equipped with a light sensitive detector (e.g., CCD, CMOS, photodiode, photomultiplier tube, film, etc.), and one or more emission or excitation filters.

In some cases, the HCP positions detected by the total protein stain and/or immunological detection reagent are observed and recorded using automated or semi-automated software. In some cases, the software can be used to identify positions by one or more of size, shape, absolute or relative position, or signal intensity. In some cases, the positions are recorded onto computer readable media for comparison to HCP positions detected by other methods, e.g., using a total protein stain. In some cases, the software can be used to observe and record "matched" HCP positions by one or more of size, shape, absolute or relative position, or absolute or relative intensity. In some cases, the software can additionally or alternatively be used to observe and record total HCP positions detected by the detection method(s) (e.g., total protein stain and/or immunological detection).

In some cases, software, such as the software described above is provided as a computer system that detects and/or records HCP positions. In some cases, the computer system is a component of an imaging device. In other cases, the computer system is a separate component from the imaging device. In some cases, the computer system compares HCP positions detected by the total protein stain to HCP positions that are immunologically detected. In some cases, the computer system determines a match rate between HCP positions detected by the total protein stain and HCP positions that are immunologically detected. In some cases, the computer system indicates whether an immunological detection reagent is validated for detection of the presence of contaminating HCPs in a biologic.

Provided herein are compositions for validation of immunological detection reagents. In some cases, the immunological detection reagents are validated for suitability as reagents for testing biological drugs. For example, the immunological detection reagents can be validated as suitable for testing biological drugs for the presence of contaminating host cell proteins or other substituents. In some cases, the immunological detection reagent is a polyclonal antibody mixture.

In some embodiments, the validation of immunological detection reagents is performed with a total protein stain. In some cases, any total protein stain can be utilized, so long as it does not interfere with subsequent immunological assays. As an example, in some cases, a total protein stain can be utilized that does not mask, or interfere with, fluorescent or chemiluminescent signals generated during a subsequent immunological detection step. As another example, in some cases, a total protein stain can be utilized that does not interfere with binding an immunological detection reagent (e.g., a polyclonal antibody mixture) during a subsequent immunological detection step. In some cases, any total protein stain can be utilized that can be removed, or substantially removed, prior to subsequent immunological detection.

In some cases, any total protein stain can be utilized so long as it is of sufficient sensitivity and meets one of the foregoing descriptions of a total protein stain that does not interfere with subsequent immunological detection. Total protein stains are sufficiently sensitive when they are capable of detecting at least about 0.1, 0.2, 0.3, 0.4, 0.5, 0.6, 0.7, 0.75, 0.8, 0.9, 1.0, 1.25, 1.5, 2, 2.5, 3, 3.5, 4, 5, 6, 7, 7.5, 8, 9, 10, 12, 14, 16, 18, 20, 25, 30, 35, 40, 45, or 50 ng or more protein in single spot, band, or position.

Exemplary embodiments of total protein stains include, but are not limited to total protein stains containing one or more of the folowing: Coomassie brilliant blue R-250 or G-250, silver stain, colloidal gold stain, zinc copper or zinc imidazole stain, or a fluorescent dye stain. Fluorescent dye stains include Sypro Ruby, Coomassie Fluor Orange, Krypton Fluorescent Protein Stain, Krypton Infrared Protein Stain, Deep Purple Stain, or Flamingo Stain. Fluorescent dye total protein stains further include metalorganic chelates such as organoruthenium chelates, including, but not limited to ruthenium II tris (bathophenanthroline), a sulfonated ruthenium II tris (bathophenanthroline), or ruthenium II tris (bathophenanthroline disulfonate. Fluorescent dye total protein stains further include azaphilones that react with primary amines to produce fluorescent compounds, or epicocconone.

In some embodiments, the membrane is contacted with a blocking agent. Suitable blocking agents include, but are not limited to one or more of the following: serum albumin, gelatin, or casein. In some cases, the serum albumin, gelatin, or casein is provided in a buffered solution. In some cases, the blocking agent includes serum or milk, e.g., non-fat milk. In still other cases the blocking agent is a protein free blocking solution containing hydrophilic or amphiphilic synthetic polymers. Other suitable blocking agents are known in the art and further suitable blocking agents can be determined empirically by contacting a membrane with a candidate blocking agent, performing immunological detection, and comparing the signal to noise provided by the immunological detection method with the candidate blocking agent as compared to other known blocking agents.

III. Systems

Provided herein are descriptions of devices, components of devices, and systems (e.g., computer systems) that may be used in the systems and methods described above.

These devices may be used, for instance, to communicate, process, and/or store data related to any of the functionalities described above. As will be appreciated by one of ordinary skill in the art, the devices described below may have only some of the components described below, or may have additional components.

In some embodiment, an immunological detection reagent can be validated, at least in part, by utilizing a management system configured to detect and record HCP positions detected using a total protein stain and an immunological detection reagent. In some cases, the system includes a computer system coupled with an imaging device. In some cases, the system includes a computer system coupled with a network. The techniques described herein are not limited to any particular type of computer system or computer network. For instance, network can be a local area network (LAN), a wide-area network (WAN), a wireless network, a bus connection, an interconnect, or any other means of communicating data or control information across one or more transmission lines or traces in an electronic system. For instance, data sources may be received manually at a user interface connected directly with computer system. Other embodiments are possible.

The computer system can include a processor and a system memory coupled together via an interconnect bus. In other embodiments, processor and system memory can be directly interconnected, or can be connected indirectly through one or more intermediary components or units. Processor and system memory can be any general-purpose or special-purpose components as is known in the art and is not limited to any particular type of processor or memory system. System memory can be configured to store system and control data for use in the embodiments described herein. Computer system may also be coupled with an imaging device, database, or filesystem (internal or external) to receive data.

In some embodiments, the computer system receives input data from the various sources at a communications interface. The computer system processes the received data and provides resulting data at its output via an output module. In a preferred embodiment, the computer system receives a first set of data values representing HCP positions detected with a non-interfering total protein stain and provides those values to the comparison engine. The computer system can receive a second set of data values representing HCP positions detected with an immunological detection reagent and provide those values to the comparison engine. The comparison engine can be configured to compare the first and second set of values to determine if the immunological detection reagent detects a sufficient number of HCPs.

Specifically, the comparison engine can be configured to compare each HCP position received in the first set of data values with a corresponding value of the second set of data values to determine whether they are present or absent. In one embodiment, if a difference is determined between the two values by the comparison engine, a signal indicating such may be asserted by the comparison engine. Similarly, in an alternate embodiment, if the two values are determined to be equal (e.g., both present or both absent), a signal indicating such can be asserted by the comparison engine. In some cases, the relative signal strength at each HCP position is also compared.

The comparison engine may be implemented using specially designed computer hardware or circuitry or general-purpose computing hardware programmed by specially designed software modules or components; or any combination of hardware and software. The techniques described herein are not limited to any specific combination of hardware circuitry or software. For instance, the comparison engine may include off-the-shelf comparator circuitry components or custom-designed comparator circuitry. The comparator circuitry is configured to compare two or more values and to output a result indicating whether the two values are equal or not equal as is well understood by skilled artisans. Alternatively, the comparison functionality may be performed in software stored in memory and executed by the processor. Exemplary embodiments of computer systems include, but are not limited to, computer systems that are configured to run Progenesis SameSpot and/or Bio-Rad PDQuest software.

All patents, patent applications, and other publications, including GenBank Accession Numbers, cited in this application are incorporated by reference in the entirety for all purposes.

IV. Examples

The following examples are provided by way of illustration only and not by way of limitation. Those of skill in the art will readily recognize a variety of non-critical parameters that could be changed or modified to yield essentially the same or similar results.

Example 1

Introduction

Biologic drugs, due to their origin/expression in genetically engineered host cells, their underlying physico-chemical properties, and the elaborate purification processes employed in their production, are subject to unique regulatory and technical requirements.

One of these requirements is the accurate monitoring and effective removal of process-derived impurities such as host cell proteins (HCP), host cell-derived DNA/RNA, viruses, cell culture media, chromatographic leachates, etc. (1). Among the different impurities, accurate monitoring of HCPs is perhaps the most challenging given that the expression system's proteome consists of thousands of different proteins, some of which can copurify with the biologic drug. The HCP monitoring method therefore, must be a multianalyte assay, with the ability to detect a great majority of the protein impurities that could be present in any batch of drug substance (2, 3).

Given its high sensitivity (low ppm) and its potential for broad specificity for the population of HCPs, enzyme-linked immunosorbant assay (ELISA) is one of the most widely used methods for monitoring HCPs (1-4). An HCP ELISA uses a polyclonal antibody reagent (anti-HCP antibodies) raised in animals against host cell protein preparations from the product expression system. The accuracy of the immunoassay depends on ability of the antibody reagent to detect essentially all, or substantially all, potential HCP impurities. Thus, the antibody reagent must be validated to be suitably specific for its intended use by testing for the percent of immunodetection it has for the total population of HCPs prior to its use in the HCP ELISA.

Among multiple technical approaches for evaluating the antibody reagent, 2-D electrophoresis and western blotting is the current gold standard for visualizing the total HCP population and assessing the percent immunocoverage of the anti-HCP polyclonal antibody reagent (5, 6). The standard workflow for this evaluation consists of four steps. First, 2-D electrophoresis (2DE) of host cell protein preparations is performed in replicate gels. Second, one gel post 2DE is processed for total protein detection via a sensitive protein stain. Third, proteins from replicate 2DE gel are transferred to a solid support membrane such as nitrocellulose or PVDF for western blotting with the polyclonal anti-HCP antibodies being evaluated. Fourth, images from 2-D electrophoresis and western blotting membrane are overlaid to obtain a match rate for determining the percentage of host cell proteins that are detectable by the anti-HCP antibodies. Although widely used, the laborious nature of this workflow and experimental variation inherent to comparisons between replicate 2DE analyses can affect overall reliability of final results. The latter in turn, complicates downstream decisions for effective HCP impurity profiling of purified biologics—including the identification of potential protein impurities missed by anti-HCP antibodies and the development of orthogonal methods to monitor these impurities.

To increase reliability of anti-HCP antibody evaluations and facilitate downstream decisions for effective HCP impurity profiling, we present here enhancements in the standard 2-D electrophoresis and western blotting workflow. Further, we apply these enhancements as a model example to the evaluation of a commercially available anti-HCP antibody reagent.

Materials and Methods

Materials

The following materials were purchased from Bio-Rad Laboratories: ReadyPrep™ 2-D cleanup kit, ReadyPrep™ rehydration/sample buffer, ReadyStrip™ IPG strips, Criterion™ gels, Trans-Blot® Turbo™ PVDF transfer packs, Bio-Safe™ Coomassie, Oriole™ fluorescent gel stain, SYPRO® Ruby protein blot stain, blotting grade-blocker, and Clarity™ Western ECL substrate. NuPage® gels were purchased from Life Technologies. Ultrafiltration protein concentration/buffer exchange cartridges were purchased from Sartorius. Cell culture media was purchased from GIBCO. Anti-HCP antibodies to CHO proteins purchased from Cygnus Technologies (3G-0016-PA) was used as primary antibody; HRP-conjugated bovine anti-goat antibody purchased from Santa Cruz Biotechnology was used as secondary antibody.

Sample Preparation

Frozen rat livers (Pel-Freez Biological) were extracted in a solution consisting of 8M Urea, 4% CHAPS, 40 mM DTT, 0.2% Bio-Lyte® ampholyte 3-10. Following extraction, sample was centrifuged at 14,000 g for 15 min and the supernatant collected for 2-D electrophoresis. These samples were used for determining influence of gel chemistry on transfer efficiency across isoelectric point (pI) and molecular weight using the Trans-Blot® Turbo™ System.

Adherent cultures of CHO-K1 cells were adapted to a medium consisting of 95% protein free defined medium (GIBCO) and 5% Ham's medium supplemented with 10% PBS. Cells were processed for collection of total protein (by sonication in 7M urea/2M thiourea and clarification by centrifugation) or secreted protein (by transferring cells to 100% protein-free defined medium). Secreted protein was prepared by 100-fold centrifugal concentration (10,000 MWCO), treated with ReadyPrep™ 2-D cleanup kit, and resuspended in 8M urea. CHO-K1 derived samples were used for 2DE&WB workflow development and evaluation of anti-CHO HCP antibodies.

2-D Electrophoresis, Protein Transfer, Total Protein Staining, and Western Blotting For rat liver samples, first-dimension separation was carried out using 11 cm pH 5-8 ReadyStrip™ IPG strips using standard IEF conditions. Second dimension separations were carried out using Novex® Bis-Tris (4-12)%, Novex® Tris-Glycine (4-12)%, Criterion® TGX™ Any kD™ or Criterion® Tris-HCl (8-16)% gels and transferred to PVDF membranes using the Trans-Blot® Turbo™ system. Following protein transfer, blots were stained with SYPRO® Ruby blot stain and visualized using a VersaDoc™ 4000 imaging system. To visualize protein remaining in the 2D gel (i.e., not transferred), gels were stained with Biosafe™ Coomassie stain and scanned on a Molecular Imager® GS800™ calibrated densitometer.

For Chinese Hamster Ovary (CHO-K1) cell derived samples, first-dimension separation was carried out using the PROTEAN® i12™ IEF cell in "gel-side up" mode with 150 μg total protein on 11cm ReadyStrip™ pH 3-10NL strips. CHO secreted sample solution was 8M Urea, 4% CHAPS, 40 mM DTT and 0.2% Bio-Lyte 3/10 carrier ampholyte; for CHO cell lysate 8M urea from preceding sample solution was replaced with 7M urea, 2M thiourea. Second dimension separations were carried out using Criterion® TGX™ Any kD™ gels.

After 2DE of CHO-K1 samples, gels were either stained with Oriole™ fluorescent gel stain or transferred to PVDF using the Trans-Blot® Turbo™ system. Following transfer, gels were stained with Oriole™ fluorescent gel stain (to visualize protein remaining on gel). Blots were stained with SYPRO® Ruby (for total protein stain) and imaged. Subsequently, they were directly processed for blocking [with 5% Blotting-grade blocker i.e., non-fat dry milk in Tris-buffered saline supplemented with 0.05% Tween-20 (TTBS)] followed by immunodetection under optimized concentrations of anti-HCP antibodies (primary antibodies diluted 1:150 in TTBS) and HRP-conjugated secondary antibodies (diluted 1:3000 in TTBS). After multiple washes (6 times for 5 min each), chemiluminescent development of western blot was performed using Clarity™ Western ECL substrate.

Image Capture and Overlay Analysis

ChemiDoc™ MP imager was used for visualization of CHO-K1 samples processed via 2-D electrophoresis (fluorescence images of stained gels and blots) and western blotting (chemiluminescent images). For image overlay analysis or spot counting, PDQuest™ 2-D analysis software was used. A 'master gel' was generated on PDQuest™ that includes all spots detected on both 2-D electrophoresis and western blotting analyses, and 'match rate' expressed as percentage determined using the following formula:

Match rate percentage=[100*(Spots detected on western blot)/(Spots detected on 'master gel')].

Results and Discussion

Factor(s) Affecting Reliability of Standard 2-D Electrophoresis and Western Blotting Workflow In designing workflow improvements for 2-D electrophoresis (2DE) and western blotting for anti-HCP antibody evaluations, we initially determined the potential for error in the standard workflow wherein replicate 2DE gels of host cell protein (HCP) preparations are processed for two analyses performed in parallel: i) total protein staining of host cell proteins on one 2DE gel and ii) western blotting (with anti-HCP antibodies) of the HCPs transferred from a replicate 2DE gel to a solid support membrane. Images from both analyses are overlaid to obtain a "match rate"—defined as the percentage of HCPs detectable by anti-HCP antibodies. However, if significant variability exists between the two replicate 2DE analyses or protein transfers post-2DE to the western blotting membrane are not efficient, then it would cause erroneous match rate estimates. Each of these factors—variability between 2DE replicates and protein transfer efficiency, thus affects reliability of final results obtained using the standard 2-D electrophoresis and western blotting workflow.

To test for the extent of potential variability between replicate 2DE gels, we initially performed three replicate 2DE analyses of identical amounts of the same quantity (150 μg) of CHO cell secreted protein and processed them further (FIG. 1). After 2DE, gels were stained with Oriole fluorescent stain similarly and processed for spot counting and matching using PDQuest™ Software under identical settings. As shown in FIG. 1 (left panels and bottom table), the 2DE replicates appear qualitatively similar and the spot number is roughly comparable between each of them (435, 449, and 454 spots, respectively).

To determine more rigorously the variability between each of the 2DE replicates, we generated a 'master gel' i.e., a virtual reference gel containing all detected spots from the three replicates, and performed overlay analysis between each of the replicates and the master gel (FIG. 1, right panels). For consistency, all images were analyzed under identical settings and no manual spot editing was done. We reasoned that if the 2DE replicates are near identical to one another, as suggested by the relatively similar number of detectable spots from each, then an overlay between the 2DE replicate and master gel should result in a near 100% match rate. However, as shown in FIG. 1 (right panels and bottom table), a significant number of detected spots on each replicate are unmatched to the master gel resulting in a 'match rate' of 70%, 72%, and 73% for each comparison. Further, the number of spots common to all three 2DE replicate analyses is even lower (289 spots; FIG. 1 bottom) pointing to significant variability between replicate 2DE analyses. These results highlight significant error potential in match rate determinations from standard workflows of 2-D electrophoresis and western blotting wherein replicate 2DE analyses are processed for total protein staining and western blotting, respectively. Thus, the use of two different (even if replicate) 2D gels should be avoided to minimize differences in spot counts from gel to gel. For reliability of final results, it would be desirable to perform total protein staining post-2DE and western blotting on the same membrane after ensuring efficient protein transfers from the 2-DE gel.

As mentioned above, efficiency of protein transfer following 2DE analysis is another important consideration for reliability of 2-D electrophoresis and western blotting results. Protein transfer efficiency can be influenced by: a) the transfer system/method used [e.g.: tank transfer system versus the much faster, semi-dry transfer/Trans-Blot® Turbo™ systems and associated buffers used] and b) SDS-PAGE gel chemistry. The speed of semi-dry transfer systems makes them an attractive option; however, it is critical that these do not compromise transfer efficiencies across the entire range of protein isoelectric points (pI) and molecular weights. Further, this evaluation needs to be performed in the context of potential influence of SDS-PAGE chemistry. Hence, we evaluated the influence of four different SDS-PAGE chemistries on transfer efficiencies using the Trans-Blot® Turbo™ system. Given the limited amount of CHO-derived material in our possession, we used rat liver lysate (as a model complex mixture of proteins with a wide range of isoelectric points and molecular weights) for these experiments described next.

Figure 2:
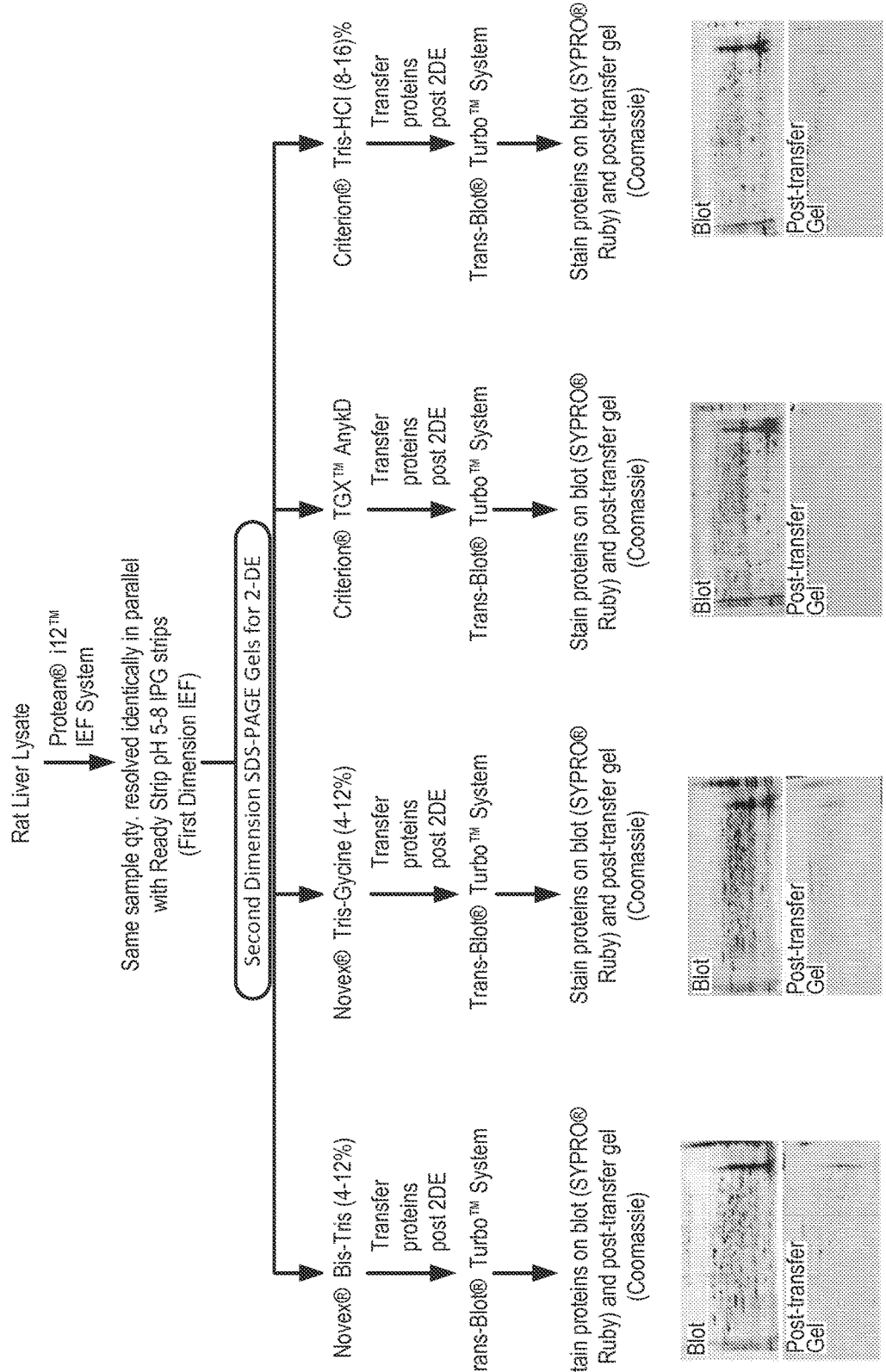
FIG. 2 depicts the effect of SDS-PAGE gel chemistry on protein transfer efficiencies post-2DE. After identical, parallel separations of rat liver lysate by first dimension IEF, samples were solved further in second dimension SDS-PAGE with the indicating gel chemistries. Subsequently all 2DE gels were processed for protein transfer using the Trans-Blot® Turbo™ system. Proteins transferred to membranes were visualized by SYPRO® Ruby staining and proteins that did not transfer were visualized by Coomassie staining of the post-transfer 2DE gels.

Identical quantities of rat liver lysate were resolved in parallel by isoelectric focusing ($1^{st}$ dimension) using pH 5-8 IPG strips (FIG. 2). Subsequently, each was resolved in the $2^{nd}$ dimension using one of the four SDS-PAGE chemistries being evaluated for effect on transfer efficiencies: Novex® Bis-Tris (4-12)%, Novex® Tris-Glycine (4-12)%, Criterion® TGX™ Any kD™, and Criterion® Tris-HCl (8-16)% gels. Following 2DE, proteins were transferred to PVDF membranes using the Trans-Blot® Turbo™ system for 7 minutes at 25V/2.5A. To visualize proteins transferred to PVDF, membranes were stained using SYPRO® Ruby and to visualize proteins remaining on each gel (i.e., not transferred to PVDF), gels were stained with Bio-Safe™ Coomassie. As shown in FIG. 2, when compared with other gel chemistries, the post-transfer Criterion® TGX™ gel has essentially no Coomassie reactive spots, indicating highly efficient protein transfer efficiency across pI and molecular weight.

The preceding results demonstrate that for reliability of final results from 2-D electrophoresis and western blotting workflow, it is desirable to perform post-2DE total protein detection and western blotting analyses on the same membrane and describe an optimal combination of SDS-PAGE gel chemistry and protein transfer systems necessary for highly efficient protein transfer post-2DE for 'same membrane' analyses.

Compatible Options for 'Same Membrane' 2-D Electrophoresis and Western Blotting Analyses Next, we considered options that might be compatible with same membrane 2DE total protein detection and subsequent western blotting. Two options were considered: (1) minimal fluorescent dye labeling (e.g. charge neutral Quasar/Cye dyes or equivalent) of HCP mixtures to be followed by chemiluminescent or fluorescent western blotting, and (2) sensitive, non-covalent protein staining (e.g. SYPRO® Ruby fluorescent stain) that is reversible and hence, compatible with western blotting applications (7).

Among the two options, fluorescent minimal dye labeling of HCP mixtures has the potential for ~5× higher sensitivity over SYPRO® Ruby staining (8). However, the former option also creates two populations of protein mixtures: those that are dye-labeled (and covalently modified resulting in slight changes to molecular weight and/or pI of the proteins) versus those that are unlabeled (and hence unmodified in terms of pI and molecular weight). This 2-fold increase in protein complexity effectively reduces the overall resolution of 2DE gels by a factor of ~2 prompting use of larger format 2DE gels. The use of large format gels extends the overall 2-D electrophoresis and western blotting workflow to ~4-5 days, requires extensive optimization for efficient protein transfer, and necessitates more careful manual handling. In addition, covalent modification of proteins (by fluorescent dye labeling) can affect their immunogenicity towards the anti-HCP antibodies, potentially influencing accuracy of the experimentally-determined match rates.

Given the limitations of dye-labeling outlined above, we preferred the second option: non-covalent, reversible staining of HCPs transferred to PVDF membranes using SYPRO® Ruby followed by western blotting with anti-HCP antibodies. We reasoned that the expected lower sensitivity of SYPRO® Ruby may be overcome by performing 2DE using a higher amount of the HCP mixture to begin with (~5-fold increase over the protein amount used with the minimal fluorescent dye-labeling option or ~150 µg protein amount for 11 cm IPG strips). In addition, since there is no effective decrease in 2DE resolution with this option, we are able to use medium-sized 2DE gel configurations optimized for fast, efficient protein transfer (11cm IPG strips, Criterion® TGX Any kD™ gels and Trans-Blot® Turbo™; FIG. 2), and a streamlined 2-D electrophoresis and western blotting workflow (~2 days total). Finally, since SYPRO® Ruby is reversible (i.e., does not covalently modify proteins (7), unlike dye-labeling), it would not affect immunogenicity of the proteins being analyzed thus enabling accurate match rate determinations.

Figure 3:
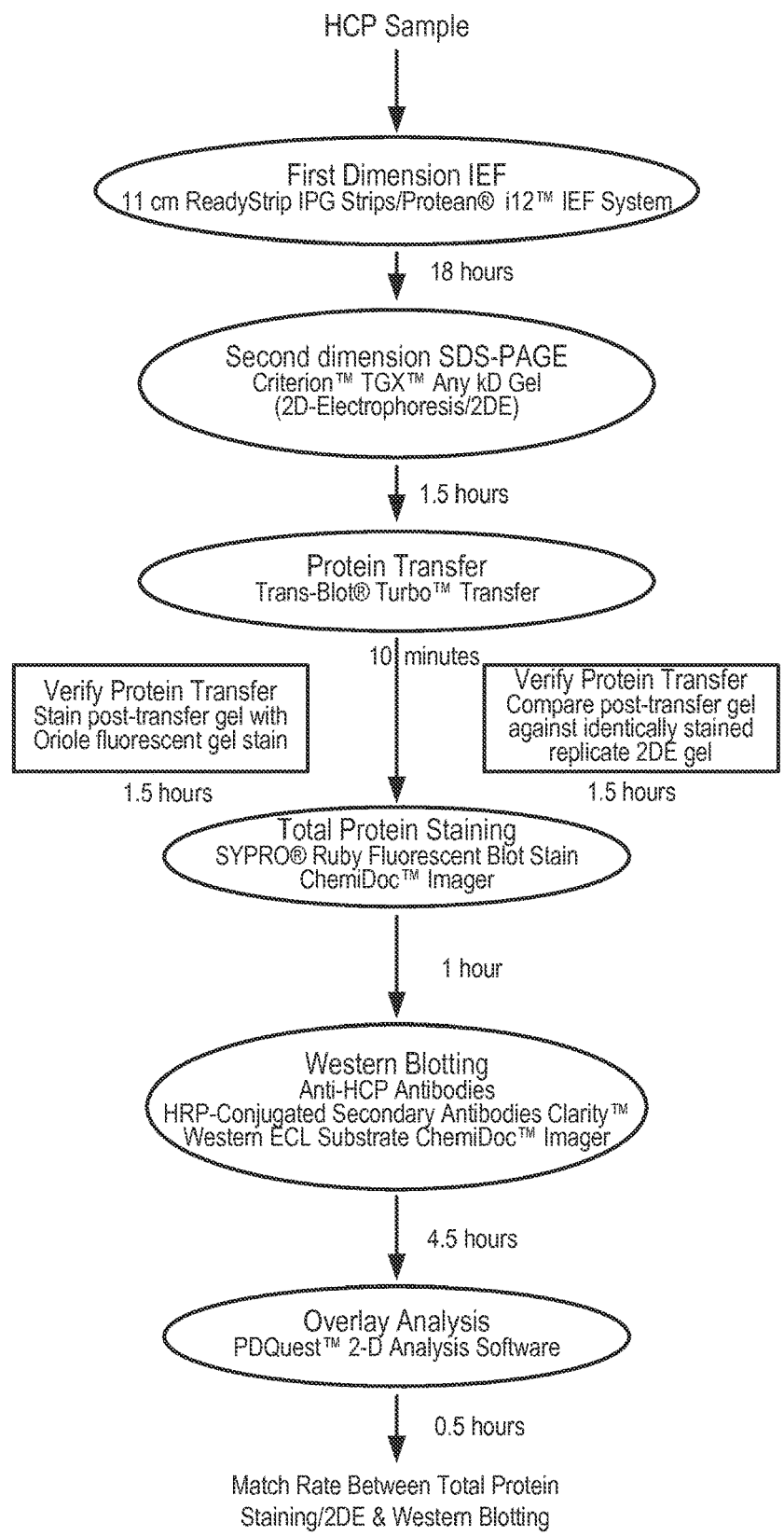
FIG. 3 depicts a workflow for evaluation of antibodies developed for detection of host cell proteins (HCPs) using a same membrane method.

Application of 'Same Membrane' 2-D Electrophoresis and Western Blotting Analyses For Evaluations of Anti-CHO HCP Antibodies Next, we employed our 2-D electrophoresis and western blotting workflow described above and outlined in FIG. 3 for evaluating a commercially available anti-CHO antibody reagent against two CHO derived samples (CHO total protein and secreted protein).

Figure 4:
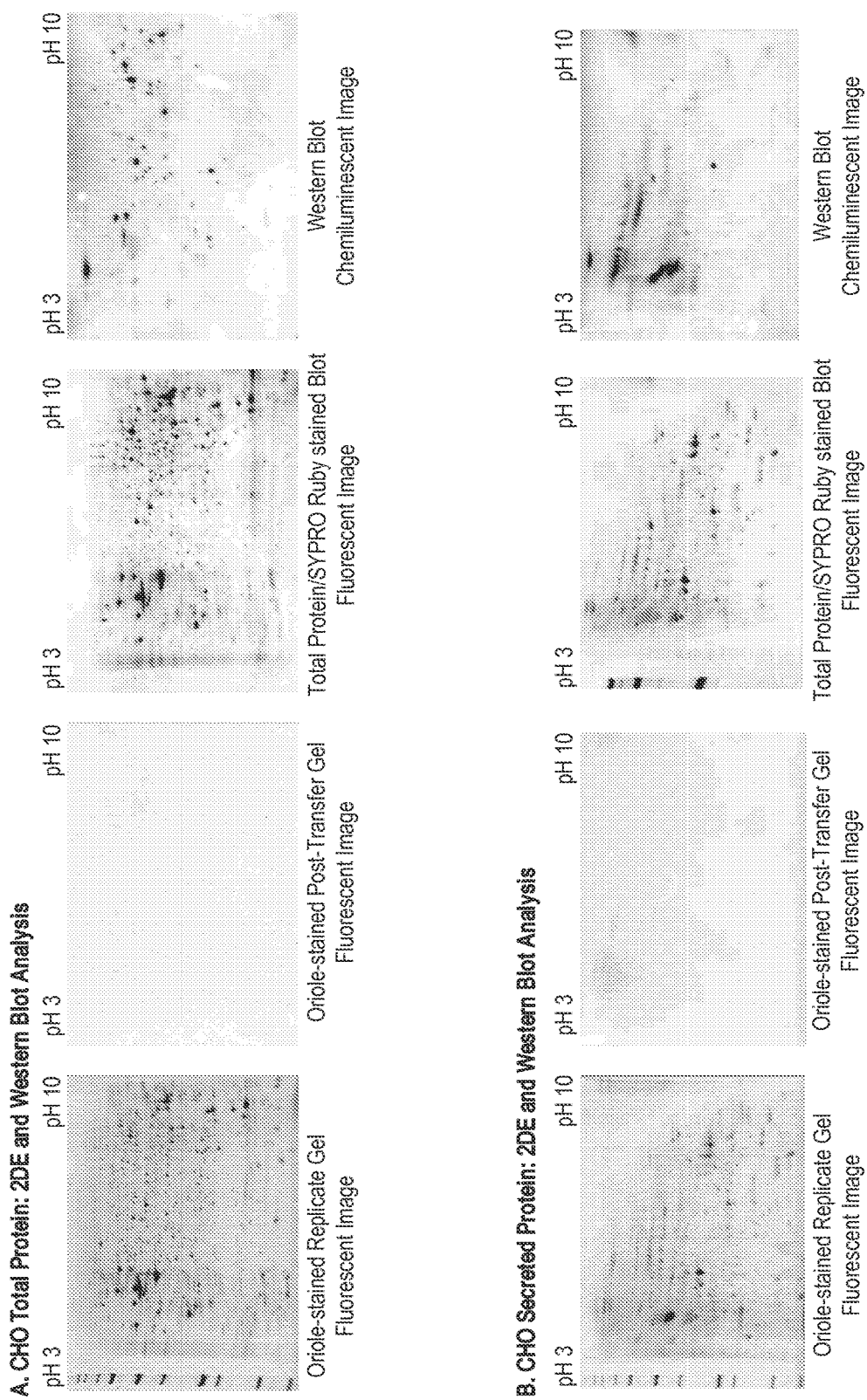
FIG. 4 depicts anti-CHO antibody evaluations using same membrane 2DE and western blotting analyses against CHO total protein (panel A) and CHO secreted protein (panel B). Protein transfer efficiencies to PVDF membranes for total protein staining and western blotting were monitored by comparing Oriole™ stained 2DE gel after transfer to a replicate 2DE gel stained similarly for each sample.

Briefly, a single 2DE analysis of each sample was performed using optimized conditions for $1^{st}$ dimension IEF (11 cm pH3-10 NL ReadyStrip™ IPG strips) and $2^{nd}$ dimension electrophoresis (Criterion® TGX™ Any kD™ gels). After 2DE, proteins were transferred to PVDF membranes using the Trans-Blot® Turbo™ in <10 minutes. To monitor efficiency of transfer, the post-transfer gel was stained with Oriole fluorescent gel stain (9) and compared against a replicate 2DE gel of each sample stained identically. Proteins transferred to PVDF were visualized by SYPRO® Ruby fluorescent protein staining and subsequently processed for chemiluminescent western blotting with anti-CHO antibodies and HRP-conjugated secondary antibodies. Images were obtained on the multi-purpose ChemiDoc™ MP imager; spot matching and image alignment were done via PDQuest™ 2-D analysis software. FIG. 4 shows images from each of the steps within the above-described workflow for 2-D electrophoresis and western blotting of CHO total protein (FIG. 4A) and CHO secreted protein (FIG. 4B) samples.

Key benefits of the workflow described herein relative to the standard 2-D electrophoresis and western blotting procedures used for anti-HCP antibody evaluations can include, but are not limited to one or more of the following: First, same membrane analysis not only overcomes reproducibility issues between 2DE replicates, but also enables high confidence spot matching and image alignment via 2-D analysis software. Second, fast (<10 minutes) highly efficient protein transfer with no detectable protein left on post-transfer gels (FIGS. 4A, 4B; compare Oriole fluorescent gel stained replicate 2DE gel versus post-transfer gel) increases thoroughness of downstream analyses. Third, fluorescent non-covalent protein staining and chemiluminescent western blotting analyses achieves high sensitivity protein detection without the loss of 2DE resolution or the potential for erroneous match rate estimates (due to modified immunogenicities of HCPs as may be seen with covalent labeling with fluorescent dyes). Fourth, the use of same imager for both analyses generates directly comparable high resolution images. Fifth, the entire workflow generates high confidence results in <2 days.

Figure 5:
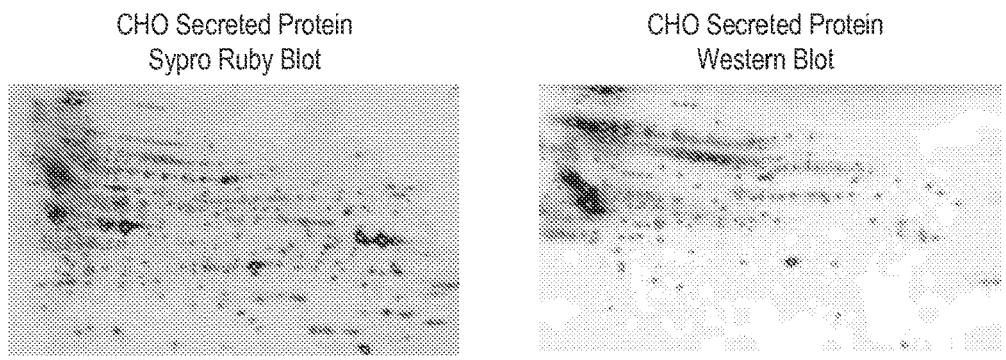
FIG. 5 depicts overlay analyses for generating match rates between total protein staining and western blotting images. Match rates were generated using the indicated formula above and PDQuest™ software for CHO secreted protein (left panel) and CHO total protein (right panel).
Figure 5:
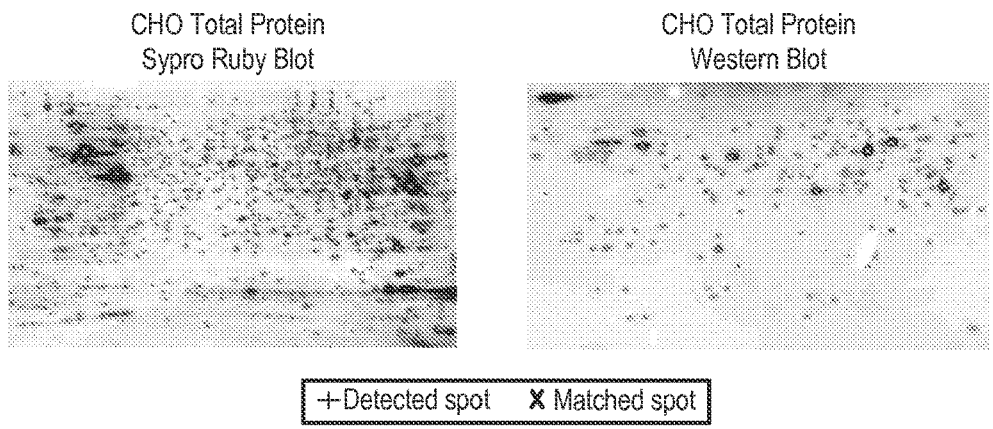

As shown in FIG. 5, a match rate of 47% was obtained using the anti-CHO HCP antibodies against CHO secreted protein versus 20% for total protein using the formula:

Match rate percentage=[100*(Spots detected on western blot)/(Spots detected on 'master gel')]

The 'master gel' includes all spots detected on both 2DE and western blotting analyses and is automatically generated using our 2-D analysis software. In theory, higher match rates can be obtained (especially for CHO secreted proteins sample) if one divided the numerator (i.e., spots detected on western blot) by only the total number of spots detected on the 2DE SYPRO® Ruby blots. However, since there are spots detected uniquely on the western blot (76 additional spots in the case of CHO secreted sample, for example; See FIG. 5 left panel) that are not seen in the total protein blot, it can be desirable to be account for these uniquely immunodetected spots in the denominator representing total proteins present in the sample. Consequently, in some embodiments, dividing the total number of spots on western blot by the total spots seen only in 2DE (i.e., SYPRO® Ruby/total protein blot in FIG. 5) for match rate estimations can be avoided and instead the formula described above adopted.

The higher match rate seen with CHO secreted protein sample versus CHO total protein sample can be expected given that the antibodies generated by the commercial vendor were against proteins released into growth medium. Using a more similar sample to that used by the vendor for antibody generation or those that are immunopurified could potentially further increase the match rate but was not done here, given our primary focus to develop needed improvements for reliable evaluations of anti-HCP antibodies. Performing these evaluations with speed and confidence is important for researchers since it enables downstream decisions on how best to monitor potential protein impurities missed by their anti-HCP antibodies/HCP ELISAs during impurity analyses of biologics.

CONCLUSIONS

We present here a streamlined 2-D electrophoresis and western blotting workflow for highly reliable evaluations of anti-HCP antibodies that can be completed in <2 days. The enhanced reliability and speed achieved in this workflow stems from the avoidance of replicate 2DE analyses, use of medium-sized IPG strips and SDS-PAGE gels, fast and highly efficient protein transfer post-2DE, and performing highly sensitive (fluorescent) total protein staining and chemiluminescent western blotting on same membrane for reliability of spot matching. In addition since the proteins remain unmodified chemically (unlike other alternatives such as fluorescent dye-labeling) there is no loss in immunogenicity of proteins towards the anti-HCP antibodies, nor is there any loss in sample resolution associated with minimal covalent labeling strategies. The latter (i.e., lack of resolution loss) also facilitates the use of medium sized 2DE gels that further accelerates the entire workflow. As proof-of-concept, our workflow was used to reliably evaluate commercially available anti-CHO HCP antibodies against CHO total protein and secreted protein samples.

REFERENCES

1. ICH Q6B: Specifications—Test Procedures and Acceptance Criteria for Biotechnological/Biological Products.
2. Leslie C. Eaton, (1995) Host cell contaminant protein assay development for recombinant biopharmaceuticals. *Journal of Chromatography A* 705, Pages 105-114.
3. Xin Wang, Alan K. Hunter, Ned M. Mozier (2009) Host Cell Proteins in Biologics Development. *Biotechnology and Bioengineering* 103, Pages 446-458.
4. Jane C Robinson (2013) Host cell protein workshop at the 2012 annual bioassay meeting of the biopharmaceutical emerging best practices association (BEBPA). *Bioanalysis* 5, Pages 407-410.
5. Edward Savino, B. H., Jason Sellers, Andrea Sobjak, Nathan Majewski, Sandra Fenton, and Tong-Yuan Yang (2011) Development of an in-house process-specific ELISA for detecting HCP in a therapeutic antibody. *Bioprocess International*, Pages 38-47.
6. Rellahan, B. (2013) Process related impurities and their impact on product quality—an FDA perspective and recommendations. *WCBP* 2013, CASSS, Washington D.C.; http://www.casss.org/associations/9165/files/Barbara%20Rellahan%20%20%20Impurities%2 04.pdf.
7. Kiera Berggren, T. H. S., Wendy M. Lauber, James A. Carroll, Mary F. Lopez, Elena Chernokalskaya, Lynn Zieske, Zhenjun Diwu, Richard P. Haugland, and Wayne F. Patton (1999) A luminescent Ruthenium complex for ultrasensitive detection of proteins immobilized on membrane supports. *Analytical Biochemistry* 276, Pages 129-143.
8. Anne Luise Tscheliessnig, J. K., Ron Bates, and Alois Junbauer (2013) Host cell protein analysis in therapeutic protein bioprocessing—methods and applications. *Biotechnology Journal* 8, Pages 1-16.
9. Tom Berkelman and John Walker. (2010) Oriole fluorescent gel stain: characterization and comparison with SYPRO Ruby gel stain. *Bio-Rad Laboratories, Technote 5921 Rev A*.

What is claimed is:

1. A method for validating an immunological detection reagent comprising a polyclonal antibody mixture for use in detection of contaminating host cell proteins (HCPs) in a biological sample, the method comprising:
    providing a biological sample containing HCPs;
    separating the HCPs by size and isoelectric point;
        transferring the separated HCPs to a membrane, thereby producing membrane-bound HCPs;
        staining membrane-bound HCPs using a non-interfering total protein stain, thereby detecting host cell protein (HCP) positions on the membrane with the non-interfering total protein stain;
        observing and recording the HCP positions on the membrane detected by the non-interfering total protein stain;
        contacting the membrane with the polyclonal antibody mixture, thereby binding antibodies from the polyclonal antibody mixture to the membrane-bound HCPs;
        detecting antibodies from the polyclonal antibody mixture bound to the membrane, thereby detecting HCP positions on the membrane with the polyclonal antibody mixture;
        observing and recording the HCP positions on the membrane detected by the polyclonal antibody mixture; and
        comparing the HCP positions detected by the non-interfering total protein stain to the positions detected by the polyclonal antibody mixture, thereby validating the polyclonal antibody mixture for use in detection of contaminating host cell proteins HCPs in a biological sample.

2. The method of claim 1, wherein the non-interfering total protein stain is substantially removed from the membrane prior to contacting the membrane with a polyclonal antibody mixture.

3. The method of claim 2, wherein the non-interfering total protein stain is substantially removed from the membrane by contacting the membrane with a blocking solution, wherein the blocking solution comprises a buffered solution of serum albumin, gelatin, or casein; serum or non-fat milk; and a protein free blocking solution containing hydrophilic or amphiphilic synthetic polymers.

4. The method of claim 1, wherein the non-interfering total protein stain detects HCP positions that contain at least about 0.25 ng to at least about 1 ng of protein on a western blot membrane.

5. The method of claim 1, wherein the non-interfering total protein stain comprises a metalorganic chelate comprising ruthenium.

6. The method of claim 5, wherein the metalorganic chelate comprising ruthenium is a sulfonated derivative of ruthenium II tris (bathophenanthroline).

7. The method of claim 6, wherein the sulfonated derivative of ruthenium II tris (bathophenanthroline) is ruthenium II tris (bathophenanthroline disulfonate).

8. The method of claim 1, wherein the observing the HCP positions on the membrane detected by the non-interfering total protein stain is performed by illuminating the membrane with electromagnetic radiation and detecting fluorescence.

9. The method of claim 1, wherein the detecting antibodies from the polyclonal antibody mixture bound to the membrane comprises contacting the membrane with a secondary detection reagent to detect bound antibodies.

10. The method of claim 9, wherein the secondary detection reagent is a secondary antibody.

11. The method of claim 10, wherein the secondary antibody is labeled.

12. The method of claim 10, wherein the secondary antibody is labeled with an enzyme, a fluorophore, a radioactive isotope, biotin, avidin, or streptavidin.

13. The method of claim 12, wherein the secondary antibody is labeled with an enzyme, wherein the enzyme is horseradish peroxidase or alkaline phosphatase.

14. The method of claim 12, wherein the secondary antibody is labeled with a fluorophore.

15. The method of claim 1, wherein the observing the HCP positions on the membrane detected by the polyclonal antibody mixture is performed by contacting the membrane with a chemiluminescent substrate and recording chemiluminescence.

16. The method of claim 15, wherein the membrane is further contacted with a chemiluminescence enhancer.

17. The method of claim 16, wherein the enhancer is 3-(phenothiazin-10-yl) propane-1-sulfonate).

18. The method of claim 1, wherein the HCP positions detected by the non-interfering total protein stain and the polyclonal antibody mixture are observed and recorded using an imaging system.

19. The method of claim 1, wherein the comparing comprises;
matching the HCP positions detected by the non-interfering total protein stain to the HCP positions detected by the polyclonal antibody mixture, wherein an HCP position is matched when they are in the same position on the western blot membrane; and
determining a match rate, wherein the match rate is the number of HCP positions detected by the polyclonal antibody mixture divided by the total number of HCP positions detectable by either the polyclonal antibody mixture or the non-interfering total protein stain.

20. The method of claim 1, wherein the polyclonal antibody mixture is validated if the ratio of HCP positions detected by the polyclonal antibody mixture to total HCP positions detected by either the non-interfering total protein stain or the polyclonal antibody mixture is at least about 0.2.

* * * * *